US012027238B2

(12) United States Patent
Erez

(10) Patent No.: US 12,027,238 B2
(45) Date of Patent: Jul. 2, 2024

(54) FUNCTIONAL PROTEIN CLASSIFICATION FOR PANDEMIC RESEARCH

(71) Applicant: GSI Technology Inc., Sunnyvale, CA (US)

(72) Inventor: Elona Erez, Tel Aviv (IL)

(73) Assignee: GSI Technology Inc., Sunnyvale, CA (US)

( * ) Notice: Subject to any disclaimer, the term of this patent is extended or adjusted under 35 U.S.C. 154(b) by 358 days.

(21) Appl. No.: 17/490,018

(22) Filed: Sep. 30, 2021

(65) Prior Publication Data

US 2022/0108772 A1 Apr. 7, 2022

Related U.S. Application Data

(60) Provisional application No. 63/086,086, filed on Oct. 1, 2020.

(51) Int. Cl.
*G16B 40/20* (2019.01)
*G06F 18/2115* (2023.01)
(Continued)

(52) U.S. Cl.
CPC .......... *G16B 40/20* (2019.02); *G06F 18/2115* (2023.01); *G06F 18/24147* (2023.01);
(Continued)

(58) Field of Classification Search
CPC ........ G16B 40/20; G16B 30/00; G16B 50/30; G06F 18/2115; G06F 18/24147;
(Continued)

(56) References Cited

U.S. PATENT DOCUMENTS 5,014,327 A 5/1991 Potter
5,799,300 A 8/1998 Agrawal
(Continued)

FOREIGN PATENT DOCUMENTS

JP 2008276344 11/2008
JP 201633806 A 3/2016
(Continued)

OTHER PUBLICATIONS

Gao X, Li G. A KNN model based on manhattan distance to identify the SNARE proteins. Ieee Access. Jun. 1, 20207;8: 112922-31. (Year: 2020).*

(Continued)

*Primary Examiner* — Fayyaz Alam
(74) *Attorney, Agent, or Firm* — HEIDI BRUN ASSOCIATES LTD.

(57) ABSTRACT

A protein searcher includes a pre-trained CNN, a feature extractor, a database and a KNN searcher. The pre-trained CNN, trained on a previously classified amino acid database, receives an unidentified amino acid sequence. The feature extractor extracts a feature vector of the unidentified amino acid sequence as a query feature vector. The database stores feature vectors of trained amino acid sequences and of at least one untrained amino acid sequence and stores associated classes of the trained amino acid sequences and associated tags of the at least one untrained amino acid sequence. The KNN searcher finds K feature vectors of the database which are close to the query feature vector and outputs the associated class or tag of each of the K feature vectors.

13 Claims, 3 Drawing Sheets

(51) Int. Cl.
*G06F 18/2413* (2023.01)
*G06N 3/04* (2023.01)
*G06N 3/08* (2023.01)
*G16B 30/00* (2019.01)
*G16B 50/30* (2019.01)

(52) U.S. Cl.
CPC .............. *G06N 3/04* (2013.01); *G06N 3/08* (2013.01); *G16B 30/00* (2019.02); *G16B 50/30* (2019.02)

(58) Field of Classification Search
CPC  G06N 3/04; G06N 3/08; G06N 3/045; G06N 20/00; G06N 3/0464; G16H 50/80
See application file for complete search history.

(56) References Cited

U.S. PATENT DOCUMENTS

| | | | |
|---|---|---|---|
| 5,983,224 | A | 11/1999 | Singh |
| 8,099,380 | B1 | 1/2012 | Shahabi |
| 8,238,173 | B2 | 8/2012 | Akerib |
| 9,418,719 | B2 | 8/2016 | Akerib |
| 9,558,812 | B2 | 1/2017 | Akerib |
| 9,859,005 | B2 | 1/2018 | Akerib |
| 10,153,042 | B2 | 12/2018 | Ehrman |
| 10,210,935 | B2 | 2/2019 | Akerib |
| 10,249,362 | B2 | 4/2019 | Shu |
| 10,402,165 | B2 | 9/2019 | Lazer |
| 10,489,480 | B2 | 11/2019 | Akerib |
| 10,514,914 | B2 | 12/2019 | Lazer |
| 10,521,229 | B2 | 12/2019 | Shu |
| 10,534,836 | B2 | 1/2020 | Shu |
| 10,635,397 | B2 | 4/2020 | Lazer |
| 10,725,777 | B2 | 7/2020 | Shu |
| 10,777,262 | B1 | 9/2020 | Haig |
| 10,832,746 | B2 | 11/2020 | Akerib |
| 10,929,751 | B2 | 2/2021 | Ehrman |
| 10,997,275 | B2 | 5/2021 | Akerib |
| 2011/0255794 | A1 | 10/2011 | Neog |
| 2013/0080490 | A1 | 3/2013 | Plondke |
| 2013/0332133 | A1 | 12/2013 | Horn |
| 2015/0332126 | A1 | 11/2015 | Hikida |
| 2016/0086222 | A1 | 3/2016 | Kurapati |
| 2016/0275876 | A1 | 9/2016 | Hagood |
| 2018/0341642 | A1 | 11/2018 | Akerib |
| 2018/0341862 | A1 | 11/2018 | Ehrman |
| 2020/0243164 | A1 | 7/2020 | Qiao |
| 2023/0063506 | A1* | 3/2023 | Salzman .............. C12Q 1/6886 |
| 2023/0368915 | A1* | 11/2023 | Abraham .............. G16H 50/20 |
| 2024/0021271 | A1* | 1/2024 | Eppler .................. G16B 20/20 |

FOREIGN PATENT DOCUMENTS

| | | |
|---|---|---|
| KR | 2014008270 | 7/2014 |
| KR | 101612605 B1 | 4/2016 |

OTHER PUBLICATIONS

Granholm, Nicolai, and Eric Tjärnstrom. "Metagenomic Classification using Machine Learning: Applied to SARS-COV-2 and Viruses." (2020). (Year: 2020).*
KNN (Year: 2020).*
Meta (Year: 2020).*
English Abstract of JP2008276344 downloaded from Google Patents on May 26, 2019.
Miller et al. "Key-value memory networks for directly reading documents." arXiv preparing arXiv: 1606.03126.
Machine Translation of Korean Publication 10-1612605 downloaded from the Korean Patent Office website on Oct. 15, 2020.
Chatzimilioudis, Distributed In-Memory Processing of All k Nearest Neighbor Queries, IEEE Transaction on Knowledge and Data Engineering, Apr. 2016.
Wohlhart, Optimizing 1-Nearest Prototype Classifiers, 2013 IEEE Conference on Computer Vision and Pattern Recognition (Year: 2013).
Maxwell L. Bileschi, et al., "Using deep learning to annotate the protein universe", bioRxiv, May 2, 2019.
International Search Report for corresponding application PCT/IB2021/058998 dated Jan. 18, 2022.
E. I. Zacharaki, "Prediction of protein function using a deep concolutional neural network ensemble", PeerJ Comput. Sci, Jul. 17, 2017.
Y. Zhang et al., "Fast Zero-Shot Image Tagging", Proc. of IEEE Conference on CVPR, pp. 5985-5994, 2016.
In-Memory Acceleration for Big data, The Linley Group, Jul. 2020.

* cited by examiner

FUNCTIONAL PROTEIN CLASSIFICATION FOR PANDEMIC RESEARCH

CROSS REFERENCE TO RELATED APPLICATIONS

This application claims priority from U.S. provisional patent application 63/086,086, filed Oct. 1, 2020, which is incorporated herein by reference.

FIELD OF THE INVENTION

The present invention relates to protein classification generally.

BACKGROUND OF THE INVENTION

A protein is composed of a sequence of amino acids, which are the building blocks of proteins. There are in total about 20 different possible amino acids.

In genetics, it is crucial to predict the function of a protein from the sequence of amino acids from which the protein is built. In order to promote advances in biotechnology, it is important to identify the proteins that catalyze novel reactions, that bind together specific microbial targets or that work together to build new molecules.

Examples of protein functions are enzymes, ligand binding proteins, membrane receptors and membrane transporters. It is crucial to annotate the function of proteins in order to understand the mechanisms of the cells in which they operate, to identify diseases that are caused by functional changes in the genes or in the proteins and to discover new tools for disease prevention, diagnosis and treatment. In pandemic research, it is important to study the genomes of the virus, such as Covid-19, causing the pandemic in order to better understand the mechanism of the disease and to improve treatment of viral infections.

DNA sequencing data of viruses is rapidly accumulated and thus there is a need to annotate, process and mine the vast data using improved or alternative gene-finding tools. Current methods are based on the BLASTp algorithm, but a large portion of microbial proteins cannot be annotated through alignment, which is the major principle of these methods. In addition, methods that are based on alignment are known to have long runtime. This approach is unscalable, because it grows with the size of the database, which by itself grows exponentially within a short time. These models are also limited by a long pipeline.

The article by Maxwell L. Bileschi, et al., "Using deep learning to annotate the protein universe", bioRxiv, 2019, has a novel approach for improving both the accuracy and the runtime of annotation algorithms and is based on deep learning methods, which have had breakthrough performance in many fields, such as computer vision and natural language processing. The article describes a "ProtCNN" deep learning system operating on proteins and having multiple "residual blocks", each based on the ResNet convolutional neural network (CNN) architecture.

The input to the neural network is a sequence of amino acids, which are represented by 20 different symbols. For example, an exemplary protein may be defined by the following sequence:

M E V F K A P P I G

In the system described in the article, each symbol in such a sequence is converted into a one-hot vector of dimension 20, according to the value of the symbol. For example, if M is defined as the $10^{th}$ type of amino acid, then its associated vector will have a 1 for the $10^{th}$ element of the vector and 0's for all the other elements. The associated sequence is the set of amino acid vectors, ordered according to the order of the protein sequence.

Before the sequence is input to the ProtCNN network, the network is trained on a large protein database, divided into training sets, test sets and development sets (i.e., to tune the hyperparameters of the network).

As is standard in neural networks, the network is trained using the training sets (i.e., sets of amino acid sequences which are annotated with their pre-classified protein functions (also known as "annotations"). At the end of the training process, the test sets are provided to the trained network. If the network is properly trained, it should output the known protein functions of the test sets. Otherwise, the test sets are used to further train the network. After this, the development sets are used to further expand the operating parameters of the trained neural network.

Various improvements are also described in the article. One of these is a combined ProtCNN-kNN combination, where the output of the ProtCNN is provided to a K nearest neighbor classification in a 'One Shot' manner. The One-Shot process is:

1) Extracting features from the ProtCNN network (i.e., the output of the network before its final layer), known as "embedding features".
2) Computing an average embedding per family of proteins used in training.
3) Performing a cosine similarity search for the embedding of an untrained protein from the dataset with the embedding features of known proteins.

The result produces the family of the untrained protein and thus, provides its annotation. As the article mentioned, this method is particularly useful for small families which have few feature vectors in the training set.

SUMMARY OF THE PRESENT INVENTION

There is therefore provided, in accordance with a preferred embodiment of the present invention, a protein searcher including a pre-trained convolutional neural network (CNN), a feature extractor, a database, and a K nearest neighbor (KNN) searcher. The pre-trained CNN is trained on a previously classified amino acid database and receives an unidentified amino acid sequence. The feature extractor extracts a feature vector of the unidentified amino acid sequence as a query feature vector. The database stores feature vectors of trained amino acid sequences and of at least one untrained amino acid sequence and stores associated classes of the trained amino acid sequences and associated tags of the at least one untrained amino acid sequence. The KNN searcher finds K feature vectors of the database which are close to the query feature vector and outputs the associated class or tag of each of the K feature vectors.

Moreover, in accordance with a preferred embodiment of the present invention, the pre-trained CNN is partially trained.

Further, in accordance with a preferred embodiment of the present invention, one of the at least one untrained amino acid sequence is from the SARS-COV-2 virus and the unidentified amino acid sequence is from a variant of the SARS-COV-2 virus.

Still further, in accordance with a preferred embodiment of the present invention, the operation being performed is a zero-shot search.

Moreover, in accordance with a preferred embodiment of the present invention, the database and the KNN searcher are implemented in an associative processing unit (APU) including a memory array to store data and to perform searches on it.

Further, in accordance with a preferred embodiment of the present invention, the memory array includes a vector section, a class section and a KNN searcher section. The vector section stores the feature vectors of trained amino acid sequences and of the at least one untrained amino acid sequence. The class section stores the associated classes and the associated tags. The KNN searcher section searches the vector section to find the K feature vectors and outputs the associated class or tag of the K feature vectors.

Further, in accordance with a preferred embodiment of the present invention, the memory array includes columns and each column stores one of the feature vectors in the vector section of the column and stores the associated class or tag of the one of the feature vectors in the class section of the column.

There is also provided, in accordance with a preferred embodiment of the present invention, a method for protein searching, The method includes having a pre-trained CNN trained on a previously classified amino acid database to receive an unidentified amino acid sequence, extracting a feature vector of the unidentified amino acid sequence as a query feature vector, storing feature vectors of trained amino acid sequences and of at least one untrained amino acid sequence, storing associated classes of the trained amino acid sequences and associated tags of the at least one untrained amino acid sequence, finding K feature vectors of the database which are close to the query feature vector, and outputting the associated class or tag of each of the K feature vectors.

Moreover, in accordance with a preferred embodiment of the present invention, the method includes partially training the pre-trained CNN.

Further, in accordance with a preferred embodiment of the present invention, one of the at least one untrained amino acid sequence is from the SARS-COV-2 virus and the unidentified amino acid sequence is from a variant of the SARS-COV-2 virus.

Still further, in accordance with a preferred embodiment of the present invention, the operation being performed is a zero-shot search.

Moreover, in accordance with a preferred embodiment of the present invention, the method includes implementing the first and second steps of storing and the step of finding in an associative processing unit (APU) including a memory array having columns divided into a vector section and a class section.

Finally, in accordance with a preferred embodiment of the present invention, the first step of storing includes storing one of the feature vectors in the vector section of one of the columns and second step of storing includes storing the associated class or tag of the one of the feature vectors in the class section of the one of the columns.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1A:
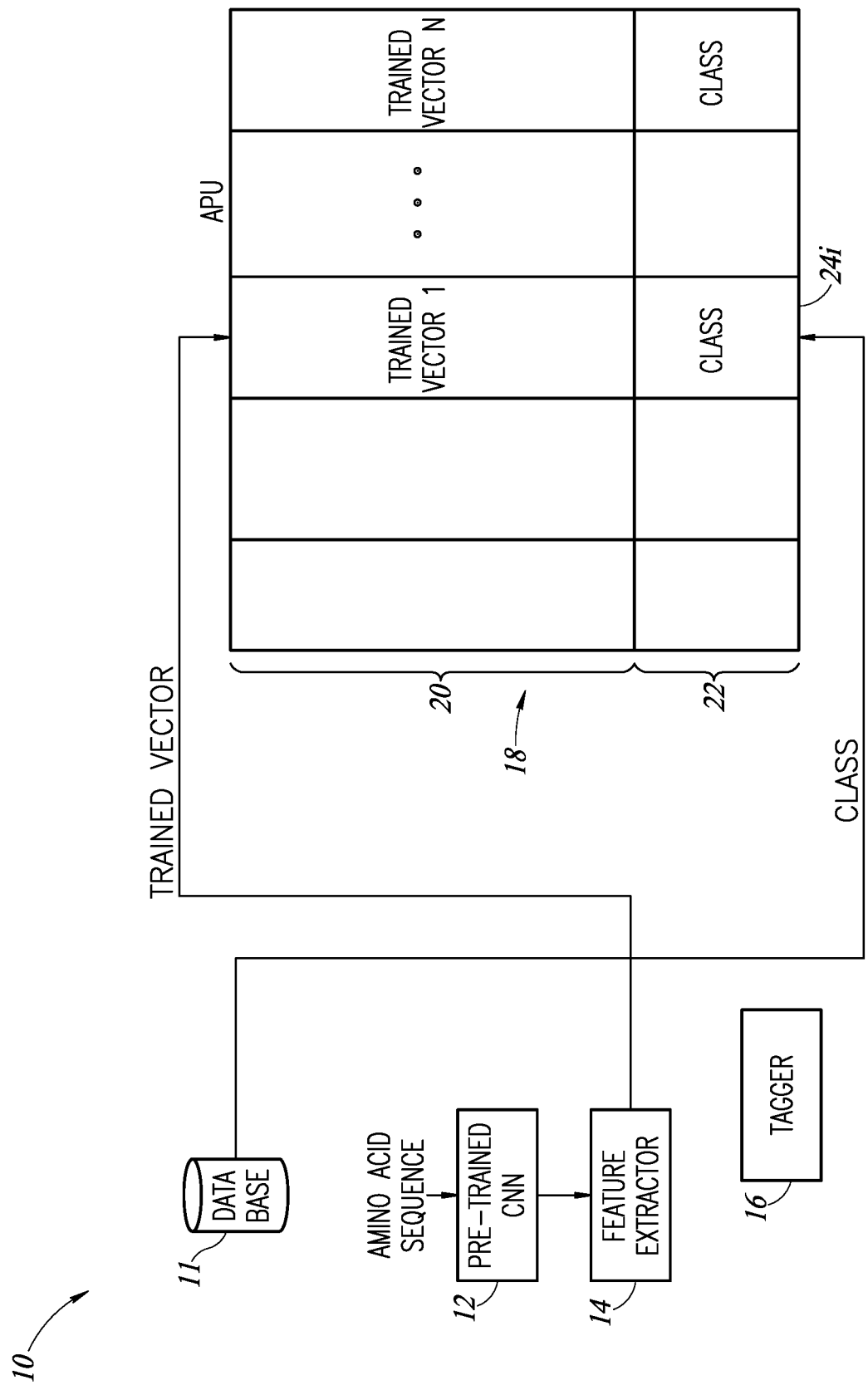
FIG. 1A is a schematic illustration of a first stage of operation of a protein search system, constructed and operative in accordance with a preferred embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Applicant has realized that, in the presence of a pandemic, such as COVID-19, speed is of the essence. The sooner proteins are functionally annotated, the sooner the genomic and protein structure of viruses and bacteria will be understood.

Applicant has also realized that deep learning approaches are significantly sped up when implemented in an associative processing unit (APU). The APU can also handle much larger databases, such as the protein databases. Moreover, Applicant has realized that the deep learning approach may be further improved by using "zero shot" learning in order to learn about proteins unseen at training time.

Figure 1B:
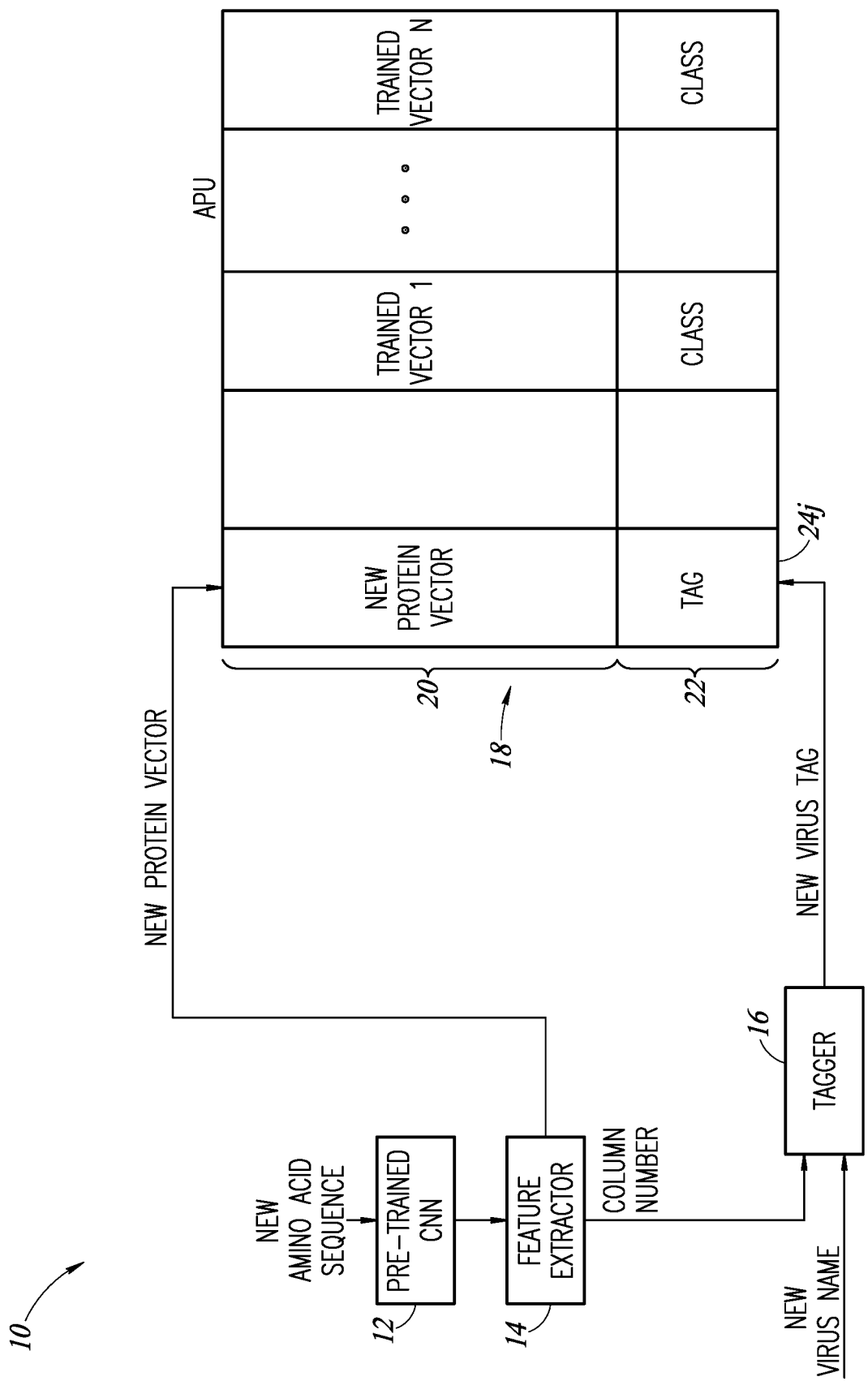
FIG. 1B is a schematic illustration of a second stage of operation of the protein search system of FIG. 1A.
Figure 1C:
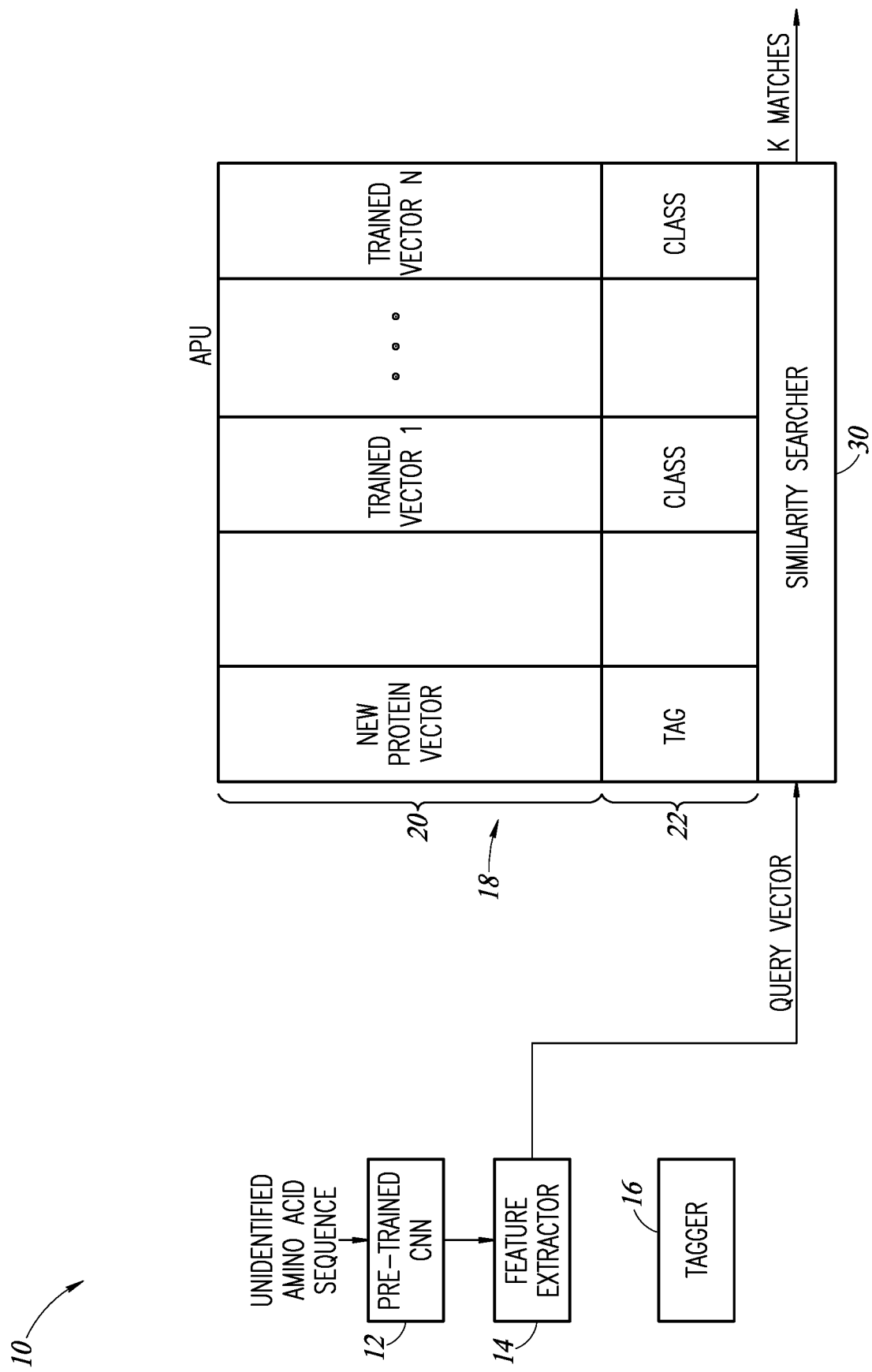
FIG. 1C is a schematic illustration of a third stage of operation of the protein search system of FIG. 1A.

Reference is now made to FIGS. 1A, 1B and 1C, which illustrate three stages of operation of a protein search system 10, constructed and operative in accordance with a preferred embodiment of the present invention. Protein search system 10 comprises a pre-trained convolution neural network (CNN) 12, a feature extractor 14, a tagger 16 and an APU 18.

APU 18 may be any suitable APU, such as the Gemini APU, commercially available from GSI Technology Inc., of California, USA, and may be formed of a memory array which is able both to store data and to perform searches on it. As shown in FIG. 1A, APU 18 may store data in its data columns 24.

Pre-trained CNN 12 may be any suitable CNN, such as the ProtCNN neural network, and may be trained on an appropriate classified protein database 11, such as the PFAM database. Pre-trained CNN 12 may receive an amino acid sequence as input from database 11 and may be trained to provide a protein class, function or annotation, also stored in database 11, as an output.

Feature extractor 14 may be any suitable feature extractor designed to extract feature vectors or "embeddings" of the trained proteins from the output of the layer before the final layer of pre-trained CNN 12, as well as the output of pre-trained CNN 12 (i.e., the protein class, function or annotation associated with the extracted feature vector).

At the initial stage of the operation of protein search system 10, database 11 may provide a plurality of amino acid sequences to pre-trained CNN 12 and their associated classes to APU 18. For each amino acid sequence, feature extractor 14 may store the extracted feature vector in a separate column 24i of APU 18. As can be seen in FIG. 1A, APU 18 may be divided into a vector section 20 storing feature vectors and a class section 22 storing classes, where each column 24i of APU 18 may store the information (feature vector and class) associated with one input amino acid sequence. For each amino acid sequence, database 11 may provide the associated class to store in its associated column 24i.

Typically, a large portion of database 11 may be provided to protein search system 10 so that their feature vectors and classes may be stored in columns 24i of APU 18. For example, APU 18 may store the 1 million feature vectors and classes generated from the PFAM database. APU 18 may also store larger databases.

In a second stage of operation and as shown in FIG. 1B, protein search system 10 may receive a new amino acid sequence, such as of a new virus, and may also receive a name of the new sequence. For example, the name of the new virus might be "COVID" or "COVID version Delta".

Protein search system 10 may provide the new amino acid sequence to pre-trained CNN 12 which may operate on it and may produce a class for it, though, since the amino acid sequence is new, it is unlikely that the generated class will be correct. Irrespective of the generated class, feature extractor 14 may extract the feature vector of the new amino acid sequence and may add it to a new column, here labeled 24j, in vector section 20 of APU 18.

Protein search system 10 may also provide the received name to tagger 16 which may generate a tag for the new virus from the received name. Feature extractor 14 may provide the column number, 24j, in which it stored the feature vector of the new amino acid sequence to tagger 16 and thus, tagger 16 may store the new virus tag in the same column, column 24j, but in class section 22.

It will be appreciated that, in the second stage shown in FIG. 1B, protein search system 10 may avoid retraining pre-trained CNN 12 when it receives a new amino acid sequence. Instead, it may use the previous training to generate embeddings for a new amino acid sequence. However, since pre-trained CNN 12 wasn't retrained, protein search system 10 may only have a tag; as the class produced by pre-trained CNN 12 will not be correct.

In a third stage of operation and as shown in FIG. 1C, protein search system 10 may receive a further new amino acid sequence which has not yet been identified, such as of a newly discovered virus, or of a newly discovered animal protein. The latter may be useful in determining how a protein evolved.

Protein search system 10 may provide the unidentified amino acid sequence to pre-trained CNN 12 which may operate on it and may produce a class for it, though, since this amino acid sequence, like the one(s) from the previous stage, is new, it is unlikely that the generated class will be correct. Irrespective of the generated class, feature extractor 14 may extract the feature vector of the unidentified amino acid sequence but, since the further new amino acid sequence is from a newly discovered source, such as a virus or animal, no tag may be generated for it.

Instead, protein search system 10 may perform a 'zero shot search' and may search the data stored in the columns 24 of APU 18 to find a match or closest neighbors to the feature vector of the unidentified amino acid sequence. In this stage, the feature vector of the unidentified amino acid sequence may act as a query vector to a similarity searcher 30 implemented in a similarity search section of APU 18 and operating on the data stored in columns 24 of feature section 20.

Thus, the first and second stages, shown in FIGS. 1A and 1B, may generate a database of feature vectors of classified proteins (FIG. 1A) and of tagged but not classified proteins (FIG. 1B). This database may be searched in the third stage (FIG. 1C). The search may be a zero-shot search, which is a search through feature vector data from a pre-trained CNN that includes data which has been classified and data which has not been classified, though it has been tagged.

For a zero-shot search, similarity searcher 30 may be a K-nearest neighbor (KNN) searcher, which may perform a similarity search using cosine, L1 or Hammond similarity measures. One exemplary similarity search is described in U.S. Pat. No. 10,929,751, entitled "Finding K Extreme Values in Constant Processing Time," dated Feb. 23, 2021, and U.S. patent application Ser. No. 16/033,259, entitled "Natural Language Processing With KNN," filed Jul. 12, 2018, published as US 2018/0341642 on Nov. 29, 2018, which are both commonly owned by the Applicant of the present invention and are incorporated herein by reference.

Similarity searcher 30 may find the K most similar vectors to the query vector from the entire database, where K may be 5, 10 or 50, or any other size significantly smaller than the size of the database, and may output the associated data (classes and/or tags) stored in class section 22 of the found vectors. Thus, protein search system 10 may determine if a newly discovered virus is of the same family as the untrained but already known virus (whose feature vector was generated in the second stage) and/or if it is similar to other amino acid sequences in the database.

It will be appreciated that, because similarity searcher 30 may be implemented in APU 18, it may be an in-memory processor and may perform its search in parallel on all columns 24. As described in U.S. Pat. No. 10,929,751, because of the parallel operation, similarity searcher 30 may have a complexity of O(1), such that the addition of further data in further columns 24 may not affect its speed of operation.

It will be appreciated that the second stage may be performed multiple times such that there may be multiple feature vectors with tags, in addition to the large plurality of feature vectors with classes from the first stage. Moreover, these additional feature vectors may not affect the speed of operation of similarity searcher 30.

Applicant has realized that pre-trained CNN 12 may be fully trained, or it may only be partially trained, as described in U.S. Pat. No. 10,929,751. In this alternative embodiment, pre-trained CNN 12 may have had its training stopped when pre-trained CNN 12 started converging (i.e., at the point that its results are beginning to be mostly correct). The remaining elements of protein search system 10 may remain the same. Thus, feature extractor 14 may extract "partially trained" feature vectors from pre-trained CNN 12 in its partially trained state, for the classified amino acid sequences, the tagged amino acid sequences and for the query amino acid sequence and similarity searcher 30 may perform its KNN search operation between the partially trained, feature vector of the query protein and the partially trained, feature vectors stored in APU 18.

It will be appreciated that, since similarity searcher 30 may be implemented on APU 18, it may find the K closest classes or functions of the query amino acid sequence in less than 1 millisecond per sequence. Moreover, protein search system 10 may avoid retraining pre-trained CNN 12, which takes a long time and a lot of computer resources, when new amino acid sequences are identified. Thus, protein search system 10 may be able to very quickly identify newly discovered virus variants.

For example, the pre-trained CNN 12 could be trained on amino acid sequences known before the SARS-COV-2 virus was discovered in December 2019, and the associated feature vectors and their classes could be stored in APU 18 (first stage). In the second stage, the amino acid sequence for SARS-COV-2 could be provided to pre-trained CNN 12 and feature extractor 14 could store that sequence's feature vector in APU 18, with the tag 'COVID-19'.

Although not mentioned hereinabove, that sequence's feature vector could be provided to similarity searcher 30 as a query vector and similarity searcher 30 could perform a search to match the new sequence to the existing ones, to find function information for the proteins in the SARS-COV-2 sequence.

In addition, when a new virus is discovered (third stage), it could be provided to protein searcher 10 to search the enlarged database to determine if the new virus is a variant of SARS-COV-2. Since similarity searcher 30 is implemented on APU 18, this whole process can be done within seconds.

It will be appreciated that, in an alternative embodiment, protein searcher 10 may utilize a database and a fast central processing unit (CPU) instead of APU 18. In this embodiment, the CPU may perform a zero-shot KNN search on the feature vector data from pre-trained CNN 12 that includes data which has been classified and data which has not been classified, though it has been tagged.

Unless specifically stated otherwise, as apparent from the preceding discussions, it is appreciated that, throughout the specification, discussions utilizing terms such as "processing," "computing," "calculating," "determining," or the like, refer to the action and/or processes of a general purpose computer of any type, such as a client/server system, mobile computing devices, smart appliances, cloud computing units or similar electronic computing devices that manipulate and/or transform data within the computing system's registers and/or memories into other data within the computing system's memories, registers or other such information storage, transmission or display devices.

Embodiments of the present invention may include apparatus for performing the operations herein. This apparatus may be specially constructed for the desired purposes, or it may comprise a computing device or system typically having at least one processor and at least one memory, selectively activated or reconfigured by a computer program stored in the computer. The resultant apparatus when instructed by software may turn the general-purpose computer into inventive elements as discussed herein. The instructions may define the inventive device in operation with the computer platform for which it is desired. Such a computer program may be stored in a computer readable storage medium, such as, but not limited to, any type of disk, including optical disks, magnetic-optical disks, read-only memories (ROMs), volatile and non-volatile memories, random access memories (RAMs), electrically programmable read-only memories (EPROMs), electrically erasable and programmable read only memories (EEPROMs), magnetic or optical cards, Flash memory, disk-on-key or any other type of media suitable for storing electronic instructions and capable of being coupled to a computer system bus. The computer readable storage medium may also be implemented in cloud storage.

Some general-purpose computers may comprise at least one communication element to enable communication with a data network and/or a mobile communications network.

The processes and displays presented herein are not inherently related to any particular computer or other apparatus. Various general-purpose systems may be used with programs in accordance with the teachings herein, or it may prove convenient to construct a more specialized apparatus to perform the desired method. The desired structure for a variety of these systems will appear from the description below. In addition, embodiments of the present invention are not described with reference to any particular programming language. It will be appreciated that a variety of programming languages may be used to implement the teachings of the invention as described herein.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A protein searcher comprising:
    a pre-trained convolutional neural network (CNN) trained on a previously classified amino acid database to receive an unidentified amino acid sequence;
    a feature extractor to extract a feature vector of said unidentified amino acid sequence as a query feature vector;
    a database to store feature vectors of trained amino acid sequences and of at least one untrained amino acid sequence and to store associated classes of said trained amino acid sequences and associated tags of said at least one untrained amino acid sequence; and
    a K nearest neighbor (KNN) searcher to find K feature vectors of said database which are close to said query feature vector and to output said associated class or tag of each of said K feature vectors.

2. The protein searcher according to claim 1 wherein said pre-trained CNN is partially trained.

3. The protein searcher according to claim 1 wherein one of said at least one untrained amino acid sequence is from the SARS-COV-2 virus and wherein said unidentified amino acid sequence is from a variant of the SARS-COV-2 virus.

4. The protein searcher according to claim 1 wherein an operation being performed is a zero-shot search.

5. The protein searcher according to claim 1 wherein said database and said KNN searcher are implemented in an associative processing unit (APU) comprising a memory array to store data and to perform searches on it.

6. The protein searcher according to claim 5 wherein said memory array comprises:
    a vector section to store said feature vectors of trained amino acid sequences and of said at least one untrained amino acid sequence;
    a class section to store said associated classes and said associated tags; and
    a KNN searcher section to search said vector section to find said K feature vectors and to output said associated class or tag of said K feature vectors.

7. The protein searcher according to claim 6 wherein said memory array comprises columns and each column to store one of said feature vectors in said vector section of said column and to store said associated class or tag of said one of said feature vectors in said class section of said column.

8. A method for protein searching, the method comprising:
- having a pre-trained convolutional neural network (CNN) trained on a previously classified amino acid database to receive an unidentified amino acid sequence;
- extracting a feature vector of said unidentified amino acid sequence as a query feature vector;
- storing feature vectors of trained amino acid sequences and of at least one untrained amino acid sequence;
- storing associated classes of said trained amino acid sequences and associated tags of said at least one untrained amino acid sequence;
- finding K feature vectors of said database which are close to said query feature vector; and
- outputting said associated class or tag of each of said K feature vectors.

9. The method according to claim 8 and comprising partially training said pre-trained CNN.

10. The method according to claim 8 wherein one of said at least one untrained amino acid sequence is from the SARS-COV-2 virus and wherein said unidentified amino acid sequence is from a variant of the SARS-COV-2 virus.

11. The method according to claim 8 wherein an operation being performed is a zero-shot search.

12. The method according to claim 8 and comprising implementing said first and second steps of storing and said step of finding in an associative processing unit (APU) comprising a memory array having columns divided into a vector section and a class section.

13. The method according to claim 12 and wherein said first step of storing comprises storing one of said feature vectors in said vector section of one of said columns and the second step of storing includes storing said associated class or tag of said one of said feature vectors in said class section of said one of said columns.

* * * * *